United States Patent [19]
Friesen et al.

[11] Patent Number: 6,136,222
[45] Date of Patent: *Oct. 24, 2000

[54] LIQUID ABSORBENT SOLUTIONS FOR SEPARATING NITROGEN FROM NATURAL GAS

[75] Inventors: Dwayne T. Friesen; Walter C. Babcock, both of Bend; David J. Edlund, Redmond; David K. Lyon; Warren K. Miller, both of Bend, all of Oreg.

[73] Assignee: Bend Research, Inc., Bend, Oreg.

[*] Notice: This patent issued on a continued prosecution application filed under 37 CFR 1.53(d), and is subject to the twenty year patent term provisions of 35 U.S.C. 154(a)(2).

[21] Appl. No.: 08/631,190

[22] Filed: Apr. 11, 1996

Related U.S. Application Data

[63] Continuation-in-part of application No. 07/805,586, Dec. 11, 1991, Pat. No. 5,225,174.

[51] Int. Cl.[7] ............................ C01B 21/06; B01D 53/14
[52] U.S. Cl. ...................... 252/184; 423/219; 423/235; 423/351; 502/34; 556/18; 556/21; 556/57; 556/146; 556/150

[58] Field of Search ................... 556/146, 57, 18, 556/21, 150; 423/235, 219, 351; 252/184; 502/34

[56] References Cited

U.S. PATENT DOCUMENTS

| | | | |
|---|---|---|---|
| 3,903,190 | 9/1975 | Pennella | 260/683.2 |
| 4,180,386 | 12/1979 | McCormack et al. | 44/63 |
| 4,251,452 | 2/1981 | McAuliffe et al. | 260/429 R |
| 4,451,270 | 5/1984 | Roman | 55/38 |
| 4,602,987 | 7/1986 | Bonaventura et al. | 204/129 |
| 4,605,475 | 8/1986 | Roberts et al. | 204/130 |
| 5,096,724 | 3/1992 | Zenner et al. | 426/124 |
| 5,393,903 | 2/1995 | Gratzel et al. | 556/137 |
| 5,516,745 | 5/1996 | Friesen et al. | 502/401 |

FOREIGN PATENT DOCUMENTS 78260   12/1970   German Dem. Rep. .

*Primary Examiner*—Joseph D. Anthony
*Attorney, Agent, or Firm*—Chernoff, Vilhauer, McClung & Stenzel, LLP

[57] ABSTRACT

Nitrogen-absorbing and -desorbing compositions, novel ligands and transition metal complexes, and methods of using the same, which are useful for the selective separation of nitrogen from other gases, especially natural gas.

14 Claims, 5 Drawing Sheets

LIQUID ABSORBENT SOLUTIONS FOR SEPARATING NITROGEN FROM NATURAL GAS

This is a continuation-in-part of application Ser. No. 07/805,586 filed Dec. 11, 1991, now U.S. Pat. No. 5,225,174.

The government has rights in this invention pursuant to Contract Nos. DE-FG-90ER80892 and DE-FG03-93ER81551 awarded by the Department of Energy.

BACKGROUND OF THE INVENTION

The non-combustible contaminant nitrogen is frequently present in natural gas, often to such an extent that the natural gas cannot be utilized as a fuel due to its low energy content and decreased environmental acceptability. For example, it has been estimated that 25% of the natural gas reserves in the United States contains unacceptably high levels of nitrogen. Thus, utilization of these natural gas reserves requires treatment to remove nitrogen.

Efforts to remove nitrogen from natural gas have included methane sorption, pressure-swing adsorption and various techniques of cryogenic distillation such as liquefaction, turbocryogenic distillation, and "cold box" separation efforts. Such methods, though successful, have been relatively expensive and inefficient. Therefore, there still exists a need for a simple, efficient and low cost method of selectively removing nitrogen from natural gas.

A substantial body of literature describes the synthesis, characterization and reactivity of transition metal-nitrogen complexes. However, the focus of this work has been substantially aimed at mimicking the ability of the enzyme nitrogenase to fix, that is reduce, nitrogen, typically to ammonia or hydrazine. See, for example, Chatt et al., 78 *Chem. Rev.* 589 (1978) and Dilworth et al., "Reactions of Dinitrogen Promoted by Transition Metal Compounds," in 3 *Comprehensive Organometallic Chemistry* 1073 (1982). Hence, the work has been aimed toward either preparing stable nitrogen complexes or identification of complexes that catalyze reduction of nitrogen, and not toward reversible nitrogen binding. Examples of such stable transition metal-nitrogen complexes are as follows:

[Fe(DEPE)$_2$(N$_2$)(H)]BPh$_4$ (DEPE=1,2-bis (diethylphosphino)ethane);

[Fe(DIPHOS)$_2$(N$_2$) (H)]BPh$_4$ (DIPHOS=1,2-bis (diphenylphosphino)ethane)

[Mo(TRIPHOS) (DIPHOS) (N$_2$)] (TRIPHOS=PhP (CH$_2$CH$_2$PPh$_2$)$_2$;

[Co(H) (N$_2$) (PR$_3$)$_3$]; and

[Ru(NH$_3$)$_5$ (N$_2$)] Cl$_2$ where R$_3$=Ph$_3$ or Me$_2$Ph, Me=methyl and Ph=phenyl).

Some complexes that are known to bind molecular nitrogen desorb the molecular nitrogen through competitive displacement. However, generally these compounds cannot rebind N$_2$; some examples include:

[Mo(N$_2$)$_2$(PPh$_2$Me)$_4$] in pyridine (Máñez et al., *JCS Dalton* 1291 (1992));

[Mo(N$_2$)$_2$(DIPHOS)$_2$ in nitriles (Carter et al., 181 *J. Organometal. Chem.* 105 (1979));

[Fe(N$_2$)(H)$_2$(PR)$_3$]BPh$_4$+CO or CH$_3$CN (Aresta et al., 5 *Inorg. Chimica Acta* 203 (1971)); and

[Ru(NH$_3$)$_5$N$_2$]Cl$_2$+pyridine, NH$_3$, dimethylsulfoxide (DMSO), Br$^-$, I$^-$ or Cl$^-$ (Allen et al., 89 *JACS* 5595 (1967)).

Reversible molecular nitrogen complexation has been demonstrated in the following solutions, but such solutions are not suitable for use in the present invention in that they have little or no selectivity for nitrogen over other gases such as hydrocarbons (e.g., methane and ethane) due to low solubility of the nitrogen complex in the solvent and in that methane is highly soluble in the solvents.

0.002 gM Ru$^{II}$ (N$_2$)(L)(TMP) in benzene (TMP=5,10,15, 20-meso tetramesitylporphyrin; L=tetrahydrofuran (THF) or CH$_3$CN) (Camenzind et al., *JCS Chem. Comm.* 1137 (1986));

0.002 gM [Ru$^{II}$ (C6-PBP)(1,5-DCI)] in toluene (C6-PBP=a strapped porphyrin, 1,5-DCI=1,5-dicyclohexylimidazole) (Collman et al., 110 *JACS* 3486 (1988));

0.07 gM Mo$^0$(N$_2$) (TRIPHOS) [PMe$_2$Ph]$_2$ in THF (TRIPHOS=(George et al., 27 *Inorg. Chem.* 2909 (1988)); and 0.01 gM Mo$^0$ (CO) (N$_2$) (DIPHOS)$_2$ in benzene (Tatsumi et al., 114 *J. Organometal. Chem.* C27 (1976)).

SUMMARY OF THE INVENTION

The present invention comprises a nitrogen-absorbing and -desorbing composition (also referred to herein as a "sorption material") and a process of using the same to selectively remove nitrogen from other gases. (The terms "nitrogen," "molecular nitrogen," dinitrogen," and "N$_2$" are used interchangeably herein to refer molecules of nitrogen reversibly bound to the transition metal complexes of the invention.)

More particularly, the sorption composition comprises a transition metal complex in a liquid capable of dissolving the transition metal complex to ≧0.1 M, the transition metal complex comprising a transition metal, and two or more ligands capable of providing four, five, or six coordinating atoms to the metal with molecular nitrogen comprising at least one of the ligands.

The process comprises absorbing molecular nitrogen from a nitrogen-containing feed stream typically containing substantially no oxygen, and no carbon monoxide, by contacting the feed stream with the nitrogen-sorption and -desorption material, followed by desorbing nitrogen from the sorption material. Desorption may be accomplished by temperature swing, pressure swing, or a combination of the two. If the nitrogen-sorption capacity decreases over time due to deactivation of the sorption material, an optional step to improve efficiency is regeneration of its nitrogen-sorption capacity by various methods.

DETAILED DESCRIPTION OF THE INVENTION

Figure 1:
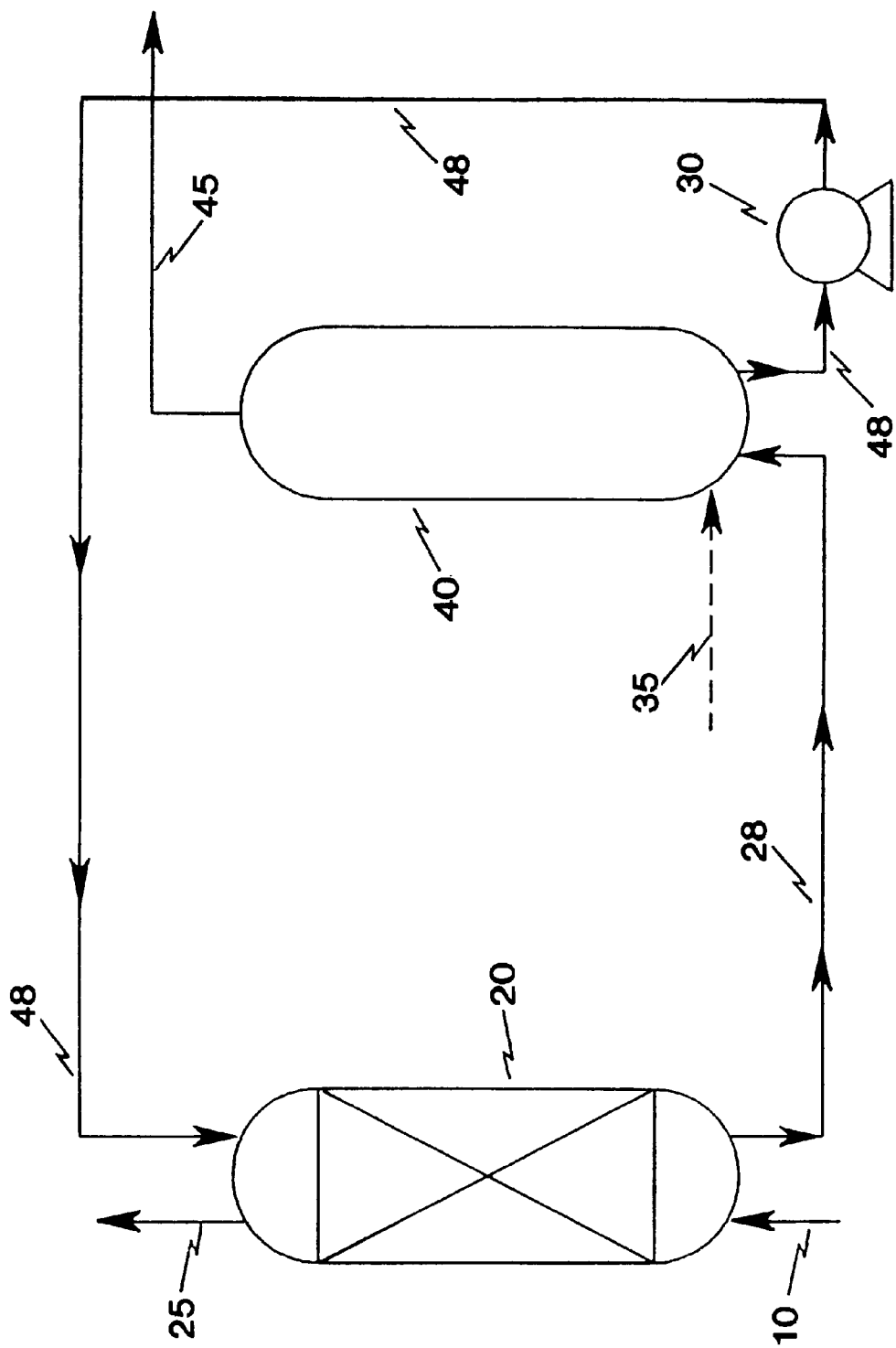
FIG. 1 is a schematic of an exemplary pressure swing absorption/desorption process of the present invention.

According to the present invention, there is provided a nitrogen-absorbing and -desorbing material having utility in the selective removal of nitrogen from a broad class of other gases and specific utility in the removal of nitrogen from naturally-occurring natural gas mixtures. The present invention is a composition comprising two essential components: a solvent; and a transition metal complex. In general terms, the solvent should:

be hydrophilic, with a solubility parameter of $\geq 20$ MPa$^{1/2}$; preferably $\geq 30$ MPa$^{1/2}$;

have a solubility limit of the transition metal complex therein $\geq 0.1$ M, preferably $\geq 0.5$ M;

be such that the methane solubility in the solution is preferably $\leq 0.1$ atm, most preferably $\leq 0.02$M/atm at 20° C.; and have low volatility (b.p. >90° C.) and low toxicity.

Generally speaking, useful solvents include liquids or mixtures of the same which are preferably polar and hydrophilic, although relatively less hydrophilic liquids may be useful in some cases. Classes of useful solvents include carbonates, phosphates, lactams, lactones, sulfides, sulfates, sulfoxides, nitriles, acids, alcohols, glycols, glycolic oligomers, diols, amides, amines, nitro-substituted alkanes, esters, ethers, and nitrogen-, oxygen-, and sulfur-containing heterocycles. Exemplary acids and esters include acetic, benzoic, and dibenzoic acids and esters thereof and 2-ethoxyethyl acetate; exemplary alcohols include substituted and unsubstituted alkanols containing 3–13 carbon atoms, cycloalkanols, and aromatic alcohols, such as propanols, butanols, pentanols, hexanols, octanols, decanols, furfuryl alcohols, cyclohexanols, phenols, benzyl alcohols and phenoxyethanol; exemplary glycols, diols and ethers include glycerol, ethylene glycol, diethylene glycol, propylene glycol, dipropylene glycol, 1,3-butane diol, 1,4-butane diol, triethylene glycol, hexylene glycol, other glycolic oligomers, 1,3-benzene diol, diacetone alcohol and ethers thereof; exemplary amines include ethanolamine and morpholine; exemplary amides include N-methylformamide (NMF), N,N-dimethylformamide (DMF), N,N-diethylformamide (DEF), N,N-dimethylacetamide (DMAC) and hexamethylphosphoramide; exemplary nitro-substituted alkanes include nitromethane, nitroethane and 2-nitropropane; exemplary nitriles include aceto-, acrylo-, propio-, butyro- and benzonitriles; exemplary lactams include 2-pyrrolidone and N-methyl-2-pyrrolidone; exemplary lactones include γ-butyrolactone and propiolactone; exemplary phosphates. include trimethyl- and tri-n-butyl-phosphate; exemplary carbonates include ethylene and propylene carbonate; exemplary sulfoxides, sulfides and sulfates include dimethylsulfoxide (DMSO), diethylsulfoxide, dimethylsulfide, diethylsulfide, dimethysulfone, dimethylsulfate and diethylsulfate; exemplary heterocycles containing nitrogen, oxygen and sulfur include pyridine, tetrahydrofuran (THF) and thiophene. Preferred solvents are water, formamide, NMF, DMF, DMAC, glycerol, glycols, such as triethylene glycol, ethylene glycol, propylene glycol, butylene glycol, monomethylethylene glycol, dimethylethylene glycol, dimethyl triethylene glycol and glycolic oligomers, and carbonates such as propylene carbonate or ethylene carbonate. Water, because of its low cost, ready availability and environmental acceptability, is especially preferred as a solvent, and may have virtually any pH, ionic strength, or salt concentration.

In the composition of the present invention, the transition metal complex is generally present at a concentration of 0.1 M or more. However, the concentration of the transition metal complex preferably does not exceed its solubility limit in the solvent at the minimum operating temperate of the nitrogen-separation system. In addition, the concentration of the transition metal complex preferably does not exceed that concentration that gives a solution viscosity of more than 100 cps at the operating temperature.

The solvent may also contain additional components that are not directly related to $N_2$ absorption and desorption that cause the process to operate more efficiently such as: antioxidants, anti-foaming agents, freezing point depression agents, surfactants, buffers, and corrosion inhibitors.

The transition metal complex comprises one or more transition metals and at least two, but not more than six, ligand(s) per transition metal. The ligand(s) must be capable of providing four, five, or six coordinating atoms to the transition metal. When the transition metal complex is equilibrated with a high activity of molecular nitrogen, for a significant fraction of said transition metal complex at least one of said ligands is molecular nitrogen. Solutions of such a transition metal complex with one or more molecular nitrogen ligands comprise the subject of this invention. The ligand(s) may be monodentate, bidentate, tridentate, tetradentate, pentadentate, or hexadentate, or any combination of mono-, bi-, tri-, tetra-, penta-, or hexadentate ligands that forms a tetracoordinate, pentacoordinate, or a hexacoordinate complex with the metal. The ligands that are coordinated to the transition metal in the transition metal complex of the present invention may be tightly coordinated or labile. As a result of ligand lability, the actual species in the absorbent solution that binds nitrogen may differ from that originally added to the solvent. In such cases the transition metal compound may only serve as a precursor to one or more active complexes. Examples of structural changes that may occur in the transition metal complex in solution include: (1) binding of solvent (as a ligand) at one or more sites, (2) exchange of solvent for bound ligands, (3) exchange of unbound ligands for bound ligands, (4) dissociation of one or more coordinating atoms of one or more ligands from the complex, (5) bridging of ligands between more than one transition metal, (6) reaction of a ligand with solvent or with an additive to the solution so that the ligand no longer functions as a ligand with respect to the transition metal (for example, protonation of a phosphine ligand to render it incapable of binding to the transition metal), and (7) rearrangement of the ligand geometry with respect to the transition metal.

As used herein, the phrase "reversible nitrogen-binding" means that the nitrogen is absorbed under conditions which are typically 0° C. to 40° C. and 2 to 30 atm nitrogen partial pressure whereby nitrogen is substantially desorbed by an increase in temperature (typically 50° C. to 120° C.) and/or a decrease in nitrogen partial pressure (typically 0.1 to 2 atm nitrogen partial pressure).

By "reversibly bound" is meant that the nitrogen-absorbing and -desorbing solution can be recycled at least five times to the absorption conditions following desorption with at least 50% of the original nitrogen-binding efficiency being retained.

The molecular nitrogen may form complexes in which one molecule of nitrogen is bound to a single transition metal complex such as in the case of $N_2$—$ML_n$ where n=1 to 5 or molecular nitrogen may be shared between two transition metal complexes such as in the case of $L_n$—M—$N_2$—$ML_n$ where n=1 to 5.

In addition, more than one molecular nitrogen may be bound to one transition metal such as in the case of

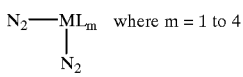 where m = 1 to 4 or molecular nitrogen may be shared between two transition metal complexes, e.g.,

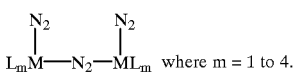 where m = 1 to 4.

Preferred reversible nitrogen-binding transition metal complexes form 1:1 $M:N_2$ or 1:2 $M:N_2$ complexes with dinitrogen. However, transition metal complexes which form 2:1 $M:N_2$ complexes or other metal-rich stoichiometries may also lead to an efficient nitrogen-removal process.

Transition metal complexes which form metal-rich/dinitrogen complexes, i.e., 2:1 $M:N_2$ complexes, may be modified to prevent the binding of two or more transition metals to one molecular nitrogen. An exemplary method that may be used to prevent the formation of metal-rich/dinitrogen complexes is the addition of sterically hindering substituents to one or more of the ligands on the metal. This addition of steric hindrance to the ligand environment can in some cases prevent more than one transition metal complex from binding to one dinitrogen molecule.

Another method that may be used to prevent the formation of metal-rich/dinitrogen complexes is to prepare electrostatically charged nitrogen-binding transition metal complexes. The electronic charge on the transition metal complexes will then repulse other similarly charged transition metal complexes, thereby preventing aggregation of the transition metal complexes around a single dinitrogen molecule.

Preferred transition metals that comprise part of the transition metal complex include the metals Cr, W, Mn, Fe, Co and Ni.

Exemplary monodentate ligands are selected from halogens and pseudohalogens (such as hydride, tetrahydridoborate, cyanide, and thiocyanate ions), arsines, stibnines, phosphines, phosphites, thiols, sulfides, thiolates, nitrogen-containing bases (including heterocycles such as pyridines, imidazoles, amides and amines), sulfur- and oxygen-containing heterocycles (such as thiophene and furans), carbon monoxide, nitrogen oxide, hydroxy, alkoxy, aryloxy, and carbanions (such as alkyl, alkenyl, alkynyl and aryl groups), whereby a metal-carbon bond is formed.

Some monodentate ligands may be homologized by covalent attachment to one or more other monodentate ligands through a bridging group to form a bidentate or multidentate ligand. These homologized monodentate ligands may contain the same donor atoms—for example, two monodentate phosphines homologized to form a diphosphine—or may contain different donor atoms. A tabulation of the suitable monodentate ligands is set forth in Table 1. Table 2 contains definitions of the R substituents of both the monodentate and the multidentate ligands, while Table 3 contains definitions of the R' bridging groups of the multidentate ligands.

TABLE 1

| Group No. | Structure | Classes of Compounds |
|---|---|---|
| 1 |  R—Z—R with R above | Amines, phosphines, arsines and stibnines where Z is N, P, As, Sb, and R is —H or as defined in Table 2, Substituent Group A, B or C |
| 2 | R—S—R | Thiols and sulfides where R is —H or as defined in Table 2, Substituent Group A, B or C |
| 3 | 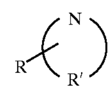 | N-containing aromatic and non-aromatic heterocycles, including substituted and unsubstituted pyrroles, pyrazines, pyrimidines, pyridines, and imidazoles where R is —H or as defined in Table 2, Substituent Group A, B or C |
| 4 |   | S- and O-containing heterocycles, including substituted and unsubstituted thiophenes, tetrahydrothiophenes, thiazoles, tetrahydrofurans, and tetrahydropyrans where R is —H or as defined in Table 2, Substituent Group A, B or C |
| 5 | RO⁻ | Hydroxy, alkoxy and aryloxy where R is —H or as defined in Table 2, Substituent Group A, B or C |
| 6 | X⁻ | Halogens and pseudohalogens where X is F⁻, Cl⁻, Br⁻, I⁻, H⁻, BH₄⁻, CN⁻, SCN⁻ or RNC⁻, and R is as defined in Table 2, Substituent Group A, B or C |
| 7 | CO, NO | Carbon monoxide or nitrogen oxide |
| 8 | R₂Z⁻ | Amides, phosphides, arsides, or stibnides where Z is N, P, As, or Sb, and R is —H or as defined in Table 2, Substituent Group A, B, or C |
| 9 | RS⁻ | Thiolates where R is H or is defined in Table 2 Substituent Group A, B, or C |
| 10 | R⁻, ⁻PhR | Carbanions such as alkyl, alkenyl, alkynyl and aryl where R is as defined in Table 2 and Ph is phenyl |

TABLE 2

| Substituent Group | Type | Definition of R |
|---|---|---|
| A | Alkyl and substitutued alkyl | 1°, 2°, 3°, and cyclic hydrocarbons containing 1 to 30 carbons where substituents are selected from halo, hydroxy, nitrile, amido, amino, mono- and dialkyl-amino, mono- and diaryl amino, mercapto, sulfonyloxy, alkoxy, thioalkoxy, aryloxy, thioaryloxy, carboxy, alkoxy-carbonyl, alkyl- and arylsulfinyl, alkyl- and arylphosphono, substituted |

TABLE 2-continued

| Substituent Group | Type | Definition of R |
|---|---|---|
| | | and unsubstituted aryls, including phenyl, biphenyl, napthyl, substituted and unsubstituted N- and S-containing heteroaryl, including pyridyl, pyrryl, piperidinyl, piperazyl, thienyl, tetrahydrothioenyl, thiazolyl groups, poly-alcohol, phenol, phenolate, carboxylic acid, carboxylate, sulfonic acid, sulfonate, sulfinic acid, sulfinate, polyether, ether, sulfoxide, sulfone, polysulfone, phosphonate, and quaternary amine |
| B | Aryl and substituted aryl | Phenyl, biphenyl, napthyl, and anthracenyl where substituents are selected from those in this Table, Substituent Group A |
| C | Heterocycles and substituted heterocycles | N-, O- and S-containing heterocycles as defined in Table 1, Groups 3 and 4, where substituents area selected from those in this Table, Substituent Group A |

TABLE 3

| Bridging Group | Type | Definition of R' |
|---|---|---|
| I | Alkylene and substituted alkylene | 1°, 2°, 3°, and cyclic hydrocarbons containing 1 to 30 carbons and at least 2 donor atoms or substituents containing donor atoms wherein the donor atoms are selected from As, C, N, O, P, S and Sb where the hydrocarbon chain that bridges the donor atoms contains 1 to 6 carbons and where substituents are selected from those in Table 2, Substituent Group A |
| II | Arylene and substituted arylene | As defined in Table 2, Substituent Group B, and containing at least 2 donor atoms or substituents containing donor atoms wherein the donor atoms are selected from As, C, N, O, P, S and Sb |
| III | Heterocycles and substituted heterocycles | As defined in Table 2, Substituent Group C, and containing at least 2 donor atoms or substituents containing donor atoms wherein the donor atoms are selected from As, C, N, O, P, S and Sb and the substituents are selected from those in Table 2, Substituent Group A |

Suitable monodentate ligands include the following groupings of compounds:

1. arsines, amines, phosphines, and stibnines of the structure

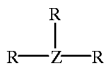

where Z is selected from As, N, P, and Sb, and each R is independently selected from —H or any of the substituents recited in Table 2, Substituent Group A, B or C (as a group, the three R substituents may comprise any combination of —H or the substituents shown in Table 2).

2. Phosphites of the structure $$P(OR)_3$$

where R is —H or as defined in Table 2.

3. thiols and sulfides of the structure

where R is H— or is as defined in Table 2.

4. halogens and the pseudohalogens $H^{31}$, $CN^-$, $BH_4^-$ and $SCN^-$.

5. carbon monoxide and nitrogen oxide.

6. thiolates of the structure

where R is H— or as defined in Table 2.

7. alkoxides of the structure

where R is H— or as defined in Table 2.

8. amides of the structure

where R is H— or as defined in Table 2.

9. phosphides, arsides, or stibnides of the structure

where Z is P, Ar, Sb, and R is H— or as defined in Table 2.

10. carbanions such as $R^-$ or $^-PhR$ where Ph is phenyl and R is as defined in Table 2.

Suitable bidentate ligands include the following groups of organic compounds:

1. amines, arsines, phosphines and stibnines of the structure

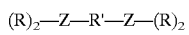

where R and Z are as defined above and R' is any of the bridging ligands set forth in Table 3.

2. phosphites of the structure

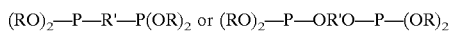

where R and R' are as defined above.

3. thiols and sulfides of the structure

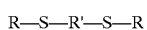

where R and R' are as defined above.

4. bidentate homologs of the substituted and unsubstituted nitrogen-, oxygen-, and sulfur-containing heterocycles as defined in Table 1, Groups 3 and 4.

5. carbamates of the structure

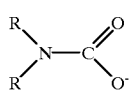

where R is as defined above.

6. thiocarbamates of the structure

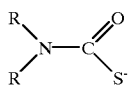

where R is as defined above.

7. dithiocarbamates of the structure

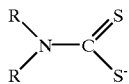

where R is as defined above.

8. thiocarbonates of the structure

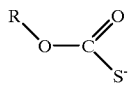

where R is as defined above.

9. dithiocarbonates and trithiocarbonates of the structure

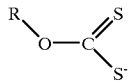 and 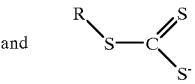

where R is as defined above.

10. dithiolenes of the structure

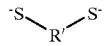

where R' is as defined above.

11. thiophosphinates of the structure

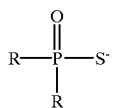

where R is as defined above.

12. dithiophosphinates of the structure

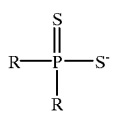

where R is as defined above.

13. diketonates of the structure

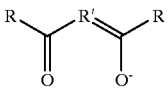

where R and R' are as defined above.

14. catecholates of the structure

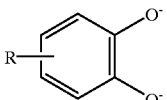

where R is as defined above.

15. carboxylates of the structure

where R is as defined above.

16. thiocarboxylates of the structure

where R is as defined above.

17. dithiocarboxylates of the structure

where R is as defined above.

18. mixed phosphine/anion ligands of the structure

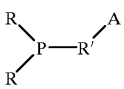

where R and R' are as defined above and A is an amide, carbanion, phosphide, alkoxide or thiolate.

Suitable tridentate ligands include the following five groups of organic compounds:

1. amines, arsines, phosphines, and stibnines having a structure selected from the following three structures

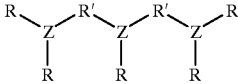

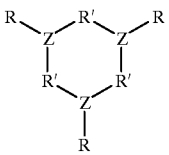

-continued

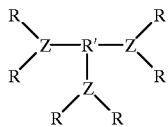

where Z, R, and R' are as defined above.

2. phosphites having a structure selected from the following two structures

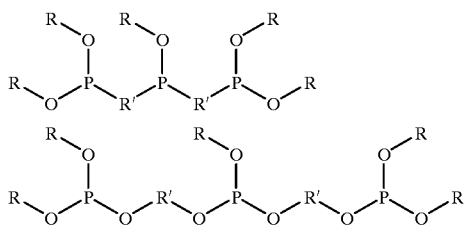

where R and R' are as defined above.

3. thiols and sulfides having a structure selected from the following two structures

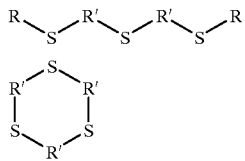

where R and R' are as defined above.

4. tridentate homologs of the substituted and unsubstituted nitrogen- and sulfur-containing heterocycles as defined in Table 1, Groups 3 and 4.

5. mixed phosphine/anion ligands of the structure

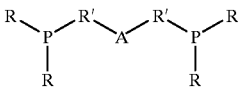

where R and R' are as defined above and A is an amide carbanion, phosphide, alkoxide or thiolate.

Suitable tetradentate equatorial ligands include the following six groups of organic compounds:

1. amines, arsines, phosphines, and stibnines having a structure selected from the following three structures

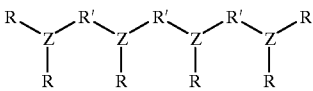

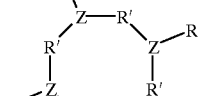

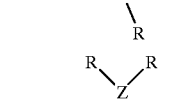

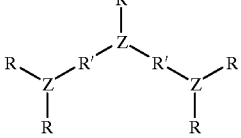

where Z, R and R' are as defined above.

2. phosphites having a structure selected from the following six structures where R and R' are as defined above.

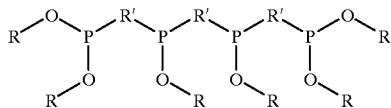

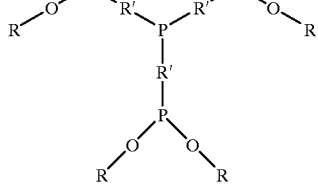

-continued

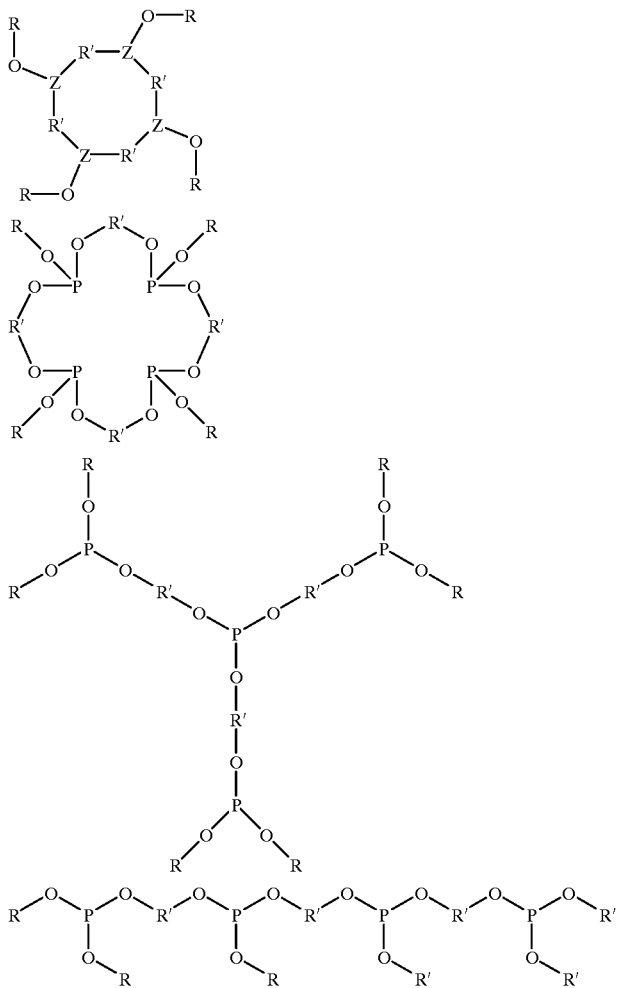

3. thiols and sulfides having a structure selected from the following two structures

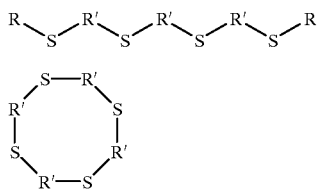

where R and R' are as defined above.

4. tetradentate homologs of the substituted and unsubstituted nitrogen- and sulfur-containing heterocycles as defined in Table 1, Groups 3 and 4.

5. substituted and unsubstituted porphyrins of the structure

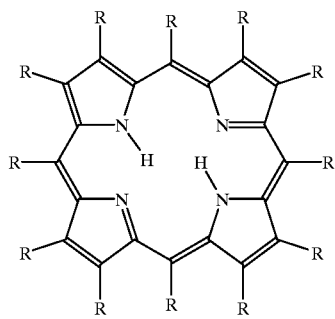

where R is as defined above.

6. substituted and unsubstituted phthalocyanines of the structure

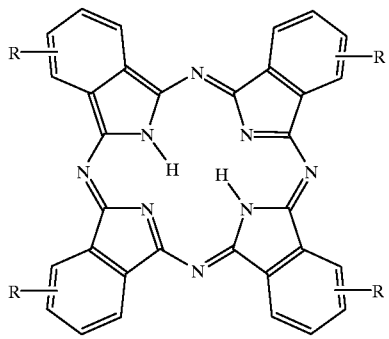

where R is as defined above.

Structural representations of preferred tetra-coordinate dinitrogen (N₂) complexes where the ligands (L), chosen from the groups discussed above, are coordinated to the metal (M) are shown below. For simplicity, these structures are represented as 1:1 metal:N₂ complexes. However, the other metal:N₂ stoichiometries mentioned above, such as 1:2 and 2:1, may also be present. These structures are represented as square planar complexes; however, other tetra-coordinate structures may also be present as well.

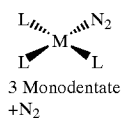

3 Monodentate
+N₂

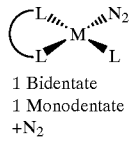

1 Bidentate
1 Monodentate
+N₂

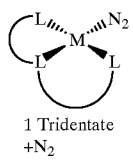

1 Tridentate
+N₂

Structural representations of preferred penta-coordinate dinitrogen (N₂) complexes where the ligands (L), chosen from the groups discussed above, are coordinated to the metal (M) are shown below. For simplicity, these structures are represented as 1:1 M:N₂ stoichiometries but the other stoichiometries mentioned above, such as 1:2 and 2:1, may also be present. These structures are represented as trigonal bipyramidal structures; however, other, penta-coordinate structures may also be present.

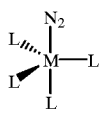

4 Monodentate
+N₂

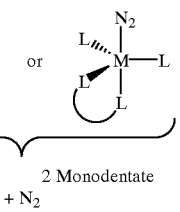

1 Bidentate     2 Monodentate
              +N₂

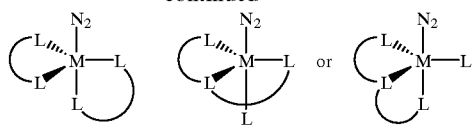

2 Bidentate        Tridentate Monodentate
+N₂                +N₂

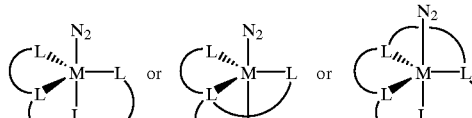

Tetradentate
+N₂

Structural representations of preferred hexacoordinate dinitrogen (N₂) complexes where the ligands (L), chosen from the groups discussed above, are coordinated to the metal (M) are shown below. For simplicity, these structures are represented as 1:1 M:N₂ stoichiometries but the other stoichiometries mentioned above, such as 1:2 and 2:1, may also be present. These structures are represented as octahedral complexes; however, other hexa-coordinate structures may also be present.

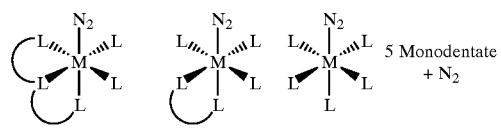

1 Tridentate            1 Bidentate + 3 Monodentate     5 Monodentate
2 Monodentate + N₂              + N₂                    + N₂

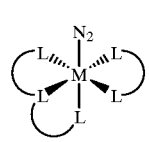

1 Tridentate, 1 Bidentate     1 Tridentate, 2 Monodentate
        + N₂                          + N₂

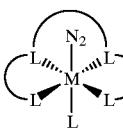

1 Tetradentate       1 Tetradentate       1 Pentadentate
1 Monodentate        1 Monodentate        1 N₂
1 N₂                 1 N₂

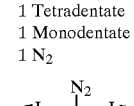

1 Pentadentate       1 Pentadentate       1 Pentadentate
1 N₂                 1 N₂                 1 N₂

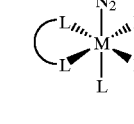

2 Bidentate +
1 Mondentate + N₂

Note that when N₂ binds, another coordinating atom may be displaced. For example, a monodentate ligand may be displaced via the reaction

ML₆+N₂⇌ML₅(N₂)+L.

Or one coordinating atom of a multidentate ligand may be displaced such as in the reaction of molecular nitrogen with a transition metal complex that contains two tridentate ligands:

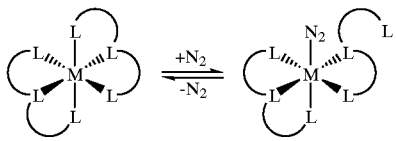

Such displacement reactions are possible for any of the ligand combinations listed above.

An especially preferred class of transition metal complexes that are useful in the absorbent solutions of the present invention comprises iron-phosphine complexes.

Preferred phosphines are highly soluble in the solvents described above. However, even moderately hydrophobic phosphines can be used in the present invention if the phosphine, in combination with a transition metal salt, yields a soluble complexes. Nitrogen-binding by iron-phosphine complexes is largely dependent upon the nature of the atoms bound directly to the iron. Thus, iron-phosphine complexes in which three or four phosphorus atoms are bound to the metal in addition to one or two other electron-donating ligands such as hydride, tetra-hydridoborate, halide or phosphine can bind nitrogen. Less important to nitrogen binding are the substituents attached to phosphorus (although alkyl and substituted alkyl phosphines can lead to superior binding). Thus, a variety of substituted phosphines can be used in conjunction with iron to lead to nitrogen-binding transition metal complexes. Monophosphines of the general structure

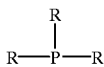

and diphosphines of the general structure

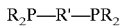

where R and R' are as defined above may be synthesized by methods that are analogous to conventional methods, such as those disclosed in Kosolapoff et al., "Organic Phosphorus Chemistry" (1972).

Exemplary methods for the preparation of monophosphines include the following two reaction schemes:

Method 1 addition of phosphine to an olefin or carbonyl-containing compound:

$$PH_3 + 3CH_2=CH-CH_2OH \rightarrow P(CH_2CH_2CH_2OH)_3$$

Initiator

Method 2 reaction of a Grignard reagent with a phosphorus trihalide:

$$3PhCH_2MgBr + PCl_3 \rightarrow P(CH_2Ph)_3$$

where Ph is phenyl or substituted phenyl.

Non-symmetric phosphines may be prepared by reaction of a Grignard reagent with an analogous phosphine compound, such as $RPH_2$, $R_2PH$, $RPCl_2$ or $R_2PCl$, where R is as defined above.

Exemplary methods for the preparation of diphosphines include the following three reaction schemes:

Method 1 addition of diphosphinoalkanes to an olefin or carboxyl-containing compound:

$$H_2P-R'-PH_2 + 4CH_2=CHCH_2OH \rightarrow (HOCH_2CH_2CH_2)_2P-R-P(CH_2CH_2CH_2OH)_2$$

Initiator where R' is as defined above.

Method 2 reaction of a Grignard reagent with bis(dihalophosphino)alkanes:

$$4PhCH_2MgBr + Cl_2P-R'-PCl_2 \rightarrow (PhCH_2)_2P-R'-P(CH_2Ph)_2$$

where Ph and R' are as defined above. The phenyl-substituted phosphines prepared in this manner may be rendered water-soluble using standard sulfonation techniques.

Method 3 reaction of two equivalents of a disubstituted phosphine with a dihaloalkane:

$$2(HOCH_2)_2PH + Cl_2R' \rightarrow (HOCH_2)_2P-R'-P(CH_2OH)_2$$

where R' is as defined above.

Two exemplary methods for preparing the iron-phosphine absorbent solutions are: (1) preparing a pre-formed complex and then dissolving it in the solvent of choice; and (2) in situ generation of an $N_2$-binding complex by reacting an iron salt and a phosphine in the chosen solvent. These two general methods are illustrated below.

Method 1

EtOH   EtOH $$FeCl_2 + 2(P_2) \rightarrow FeCl_2(P_2)_2 + NaBH_4 \rightarrow Fe(H)(Cl)(P_2)_2$$

where $P_2$ is bis [di-(4-hydroxybutyl)phosphino]ethane (HOBuPE).

Subsequently, dissolution of the complex in a solvent such as water or an alcohol such as triethylene glycol leads to an $N_2$-binding solution.

Method 2

$H_2O$ $$FeA_2 + 2 \text{ HOBuPE} \rightarrow [Fe(H_2O)_2(HOBuPE)_2 \bullet 2A]$$

where A is a weakly coordinating anion and HOBuPE is as defined above.

The nitrogen sorption material may be used in any of a pressure swing absorption (PSA) process, a temperature swing absorption (TSA) process or a hybrid combination process of PSA and TSA. In general, it is preferably used in a PSA/TSA mode. In a PSA/TSA mode, the difference in nitrogen partial pressures between the absorption and desorption steps is preferably in the range of 10 to 400 psi. The preferred temperature differential is in the range of 20 to 100° C. for economic efficiency to be realized. Nitrogen partial pressure in the desorption step may also be reduced by the use of an inert sweep gas, such as $H_2O$ (steam), carbon dioxide, argon, hydrogen, helium or methane, preferably in a countercurrent flow mode. Sweep gas may also effectively be generated in situ by the release of other gases (such as methane or other hydrocarbons) absorbed in the solution or by generation of solvent vapor through evaporation; this release of other sorbed gases effectively lowers the partial pressure of nitrogen. In terms of total pressure, the absorption step is preferably conducted at a total pressure that is at least five times the total pressure of the desorption step.

The feed gas preferably comprises a mixture of nitrogen and other gases, typically methane and other hydrocarbons, the mixture preferably containing essentially no oxygen, and no carbon monoxide. Preferred limits on such impurities are such that the partial pressures of the gases are as follows: oxygen $\leqq 1$ psi, more preferably $10^{-3}$ psi; and carbon monoxide $\leqq 10$ psi. Notwithstanding these preferred limits, in some cases the nitrogen sorption material may be unaffected by the presence of such impurities and so the feed gas may contain substantial amounts, say, up to 10 vol %, of the same. In addition, the preferred nitrogen absorbent will be essentially non-reactive toward carbon dioxide, hydrogen sulfide, methyl mercaptan, and other non-nitrogen components found in hydrocarbon gas feed streams. The feed may be at virtually any temperature in the range of −20° C. to 100° C. although in certain cases, mentioned below, higher temperatures may also be used. In general, the preferred temperature range is 0° C. to 40° C. The amount of nitrogen in the feed stream may be anywhere from 0.1 to 80 vol %. Nitrogen may be mixed with virtually any other gas or-combination of gases with the restrictions on impurities noted above. Preferred applications include mixtures of nitrogen with hydrocarbons containing from 1 to 7 carbons, including natural gas, and with hydrocarbons from partial oxidation of hydrocarbons containing from 1 to 7 carbon atoms (from the oxidation of coal and from the oxidative coupling of hydrocarbons). The feed may be fed at a pressure of anywhere from 20 psig to 2000 psig, but preferably no higher than 1400 psig.

Over time the nitrogen-sorbing capacity of the solution may decrease by any of a variety of mechanisms, including reaction of the transition metal complex with the solvent or an impurity in the gaseous feedstream. The nitrogen-absorbing capability of the solution may be periodically regenerated by a variety of techniques, including:

(1) heating the solution to 30° C. to 180° C. while avoiding oxidizing conditions, preferably in the presence of relatively pure nitrogen or a reducing agent such as hydrogen, magnesium, iron or thiosulfate ion;

(2) stripping the solvent from the solution and then recrystallizing the residual transition metal complex from a suitable solvent under a nitrogen or other inert gas atmosphere; and (3) demetallating the transition metal complex in solution by the addition of a strong acid, extracting the oxidized transition metal into an immiscible organic solvent, then coordination of the reduced transition metal with the solution of the ligand(s) and isolating the regenerated organometallic complex.

In connection with the first regeneration method mentioned above, oxidizing conditions may be avoided by heating the solution (a) under a vacuum of from 0.0001 to 500 torr for about 1 to 48 hours, (b) in an atmosphere of a coordinating gas such as-nitrogen or an inert gas such as argon for about 1 to 72 hours, or (c) in a reducing atmosphere such as hydrogen for from about 1 to 72 hours, with or without the presence of a reduction catalyst such as a platinum group metal.

In connection with the second regeneration method, the inactive transition metal complex may be isolated from the solvent by vacuum or atmospheric distillation of the solvent, and the residual transition metal complexes recrystallized from an appropriate solvent.

In connection with the third method of regeneration, suitable strong acids include hydrochloric acid, sulfuric acid, and trifluoroacetic acid. The oxidized metal may be extracted into an immiscible organic solvent, such as toluene or other aromatic solvents, or hexane or other aliphatic solvents, by addition of an organic-soluble metal extractant, such as dialkylphosphoric acids, alkylamines, quaternary alkylamines, and alkyl-β-diketones, to the aromatic or aliphatic solvent. Suitable solvents for recrystallization of the transition metal include water, methanol, ethanol, tetrahydrofuran, and acetonitrile.

Referring now to the drawings, wherein like numerals refer to the same elements, use of the solution of the present invention in a PSA mode is depicted in FIG. 1. There, a nitrogen-containing feed 10 is introduced into a conventional gas-liquid absorption column 20 so that the gas is efficiently contacted with the solution of the present invention. Within the absorption column 20, nitrogen is selectively absorbed by the solution, resulting in a reduction in the nitrogen concentration in the "product" gas 25 exiting the column (it being understood that virtually any gas other than nitrogen, depending upon the desired separation, could be regarded as the product gas). The residence time of the solution in the absorption column 20 is on the order of a few minutes and generally should be sufficiently long to achieve nitrogen binding to at least 10 mol % of the transition metal-based complex. The column should be sized sufficiently to accommodate the requisite volume and flow rate of liquid absorbent to have sufficient contact time for nitrogen to be absorbed by the liquid. In place of the absorption column 20, other gas-liquid contactors may be utilized, such as membrane contactors in the form of hollow fiber modules. The nitrogen-complexed liquid absorbent 28 is passed to a desorption column 40 in which nitrogen is desorbed from the liquid absorbent. For nitrogen desorption to occur in the desorption column, the partial pressure of nitrogen in the nitrogen-containing stream 45 exiting the desorption column 40 must be less than the partial pressure of nitrogen in the product stream 25 exiting the absorption column 20. This condition is met by operating the desorption column 40 at a reduced pressure relative to the absorption column 20 (typically near 0 psig total pressure) or by using a sweep stream 35 to maintain low nitrogen partial pressures in the nitrogen-containing stream 45 exiting the desorption column 40. The nitrogen-containing stream 45 desorbed from the liquid absorbent exits the desorption column. 40 at substantially the same pressure as that prevailing in the desorption column, which is typically near 0 psig total pressure. In some cases the desorbed nitrogen from the nitrogen-containing stream 45 may be the end product of the separation process. After nitrogen is desorbed from the liquid absorbent in the desorption column 40, the nitrogen-desorbed liquid absorbent 48 is returned to the absorption column 20 by use of a pump 30 and the cycle is repeated.

Figure 2:
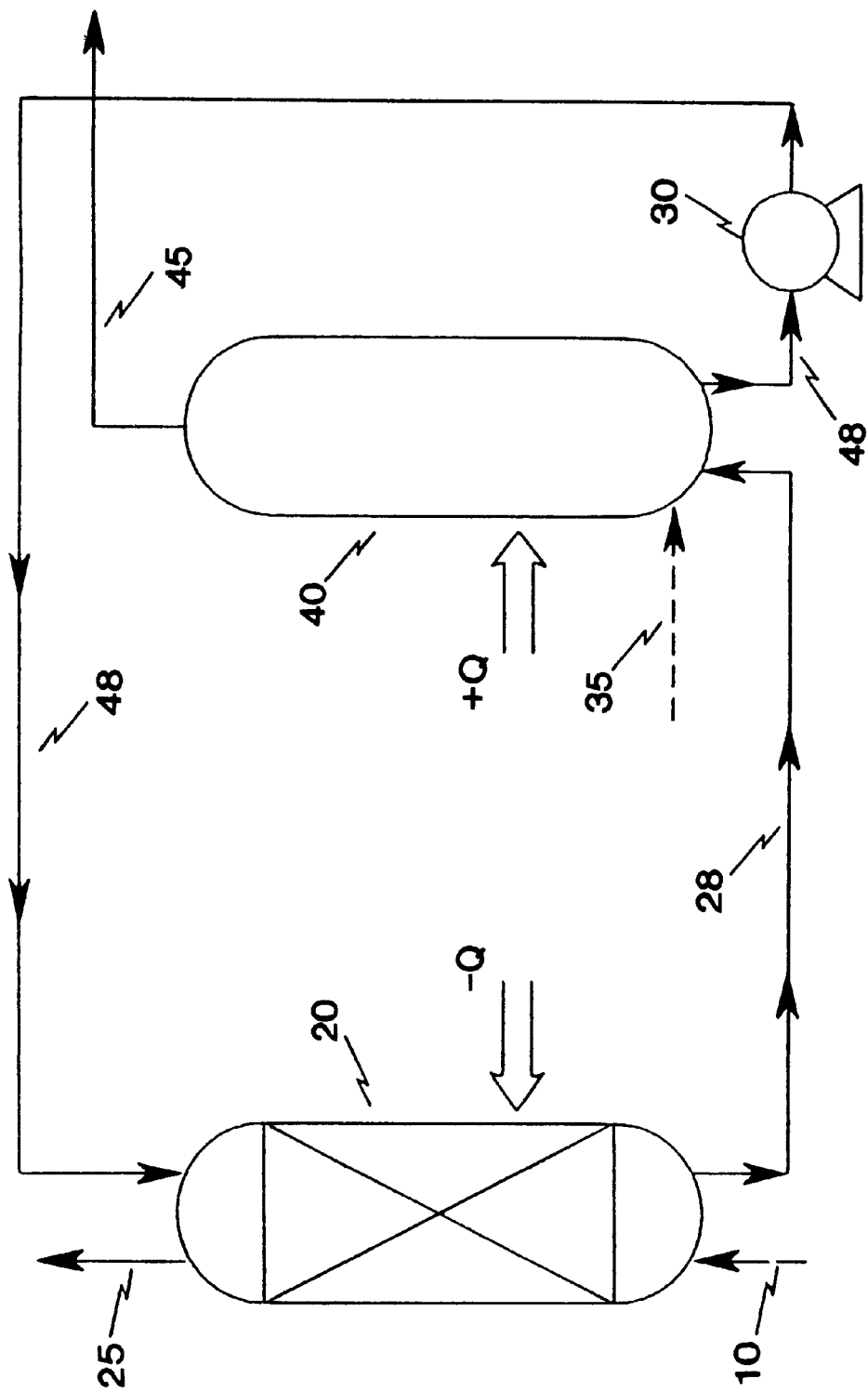
FIG. 2 is a schematic of an exemplary hybrid pressure/temperature swing absorption/desorption process of the present invention.

Use of the nitrogen-sorbing and -desorbing solution of the present invention in a hybrid PSA/TSA mode is shown schematically in FIG. 2. There, the system is operated in generally the same manner as described for FIG. 1, except that the desorption column 40 is operated at an elevated temperature-relative to the absorption column 20, the addition of heat to the desorption column 40 being depicted schematically by the symbol "+Q." Alternatively, the absorption column 20 may be cooled relative to the desorption column 40, this being schematically depicted by the symbol "−Q." This hybrid mode of operation is useful in compensating for the fact that the nitrogen-binding capacity of the liquid absorbent for a given nitrogen partial pressure decreases with increasing temperature inasmuch as the nitrogen-binding is typically a somewhat exothermic reaction. As a result, the nitrogen partial pressure in equilibrium with the nitrogen-containing absorbent will increase with increasing temperature. For nitrogen desorption to occur in the desorption column 40, the concentration in the absorbent liquid in equilibrium with product gas 25 exiting the absorption column 20 at the temperature and pressure prevailing therein must exceed the concentration of nitrogen in the absorbent in equilibrium with the nitrogen in nitrogen-containing stream 45 at the temperature and pressure prevailing in the desorption column 40. The advantage of the hybrid PSA/TSA mode over the purely PSA mode is that in the former, nitrogen desorption can be achieved in the desorption column 40 at nitrogen partial pressures greater than those allowed in the strictly PSA mode. As with the PSA mode, the hybrid PSA/TSA mode may be used to achieve nitrogen desorption in the desorption column 40 by either operating the desorption column at reduced pressure relative to the absorption column or by the use of a sweep gas. However, since the desorption column is at a higher temperature than the absorption column, the desorption column need not be at a lower pressure but may be at the same or even higher pressure than the absorption column. Another advantage of operating the desorption column at elevated temperature is that an increase in the rate of nitrogen desorption from the liquid absorbent occurs, resulting in a decrease in the residence time required for the liquid absorbent in the desorption column.

Figure 3:
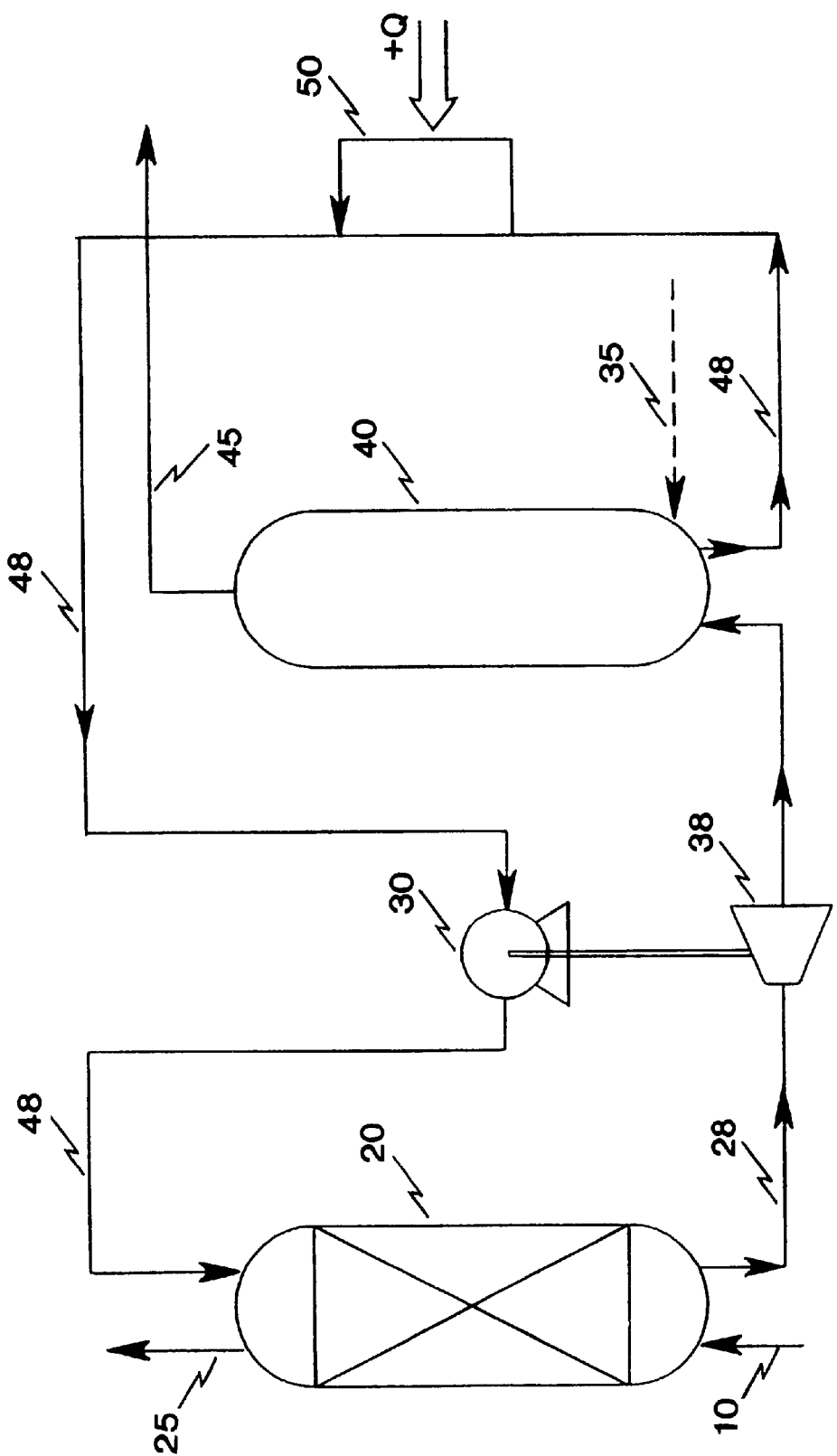
FIG. 3 is a schematic of the exemplary process depicted in FIG. 1 wherein a pressure-reducing turbine and a regeneration loop are included.

FIG. 3 depicts the inclusion of a regeneration loop 50 wherein the nitrogen-desorbed liquid sorbent 48 is treated by one of the methods described above to regenerate its nitrogen-sorption capacity as well as the inclusion of a pressure-reducing turbine 38 to recover energy otherwise lost, the energy being used to drive the liquid pump 30. A preferred type of pressure-reducing or power recovery turbine is that which is commercially available from Sulzer Bingham of Portland, Oreg.

Figure 4:
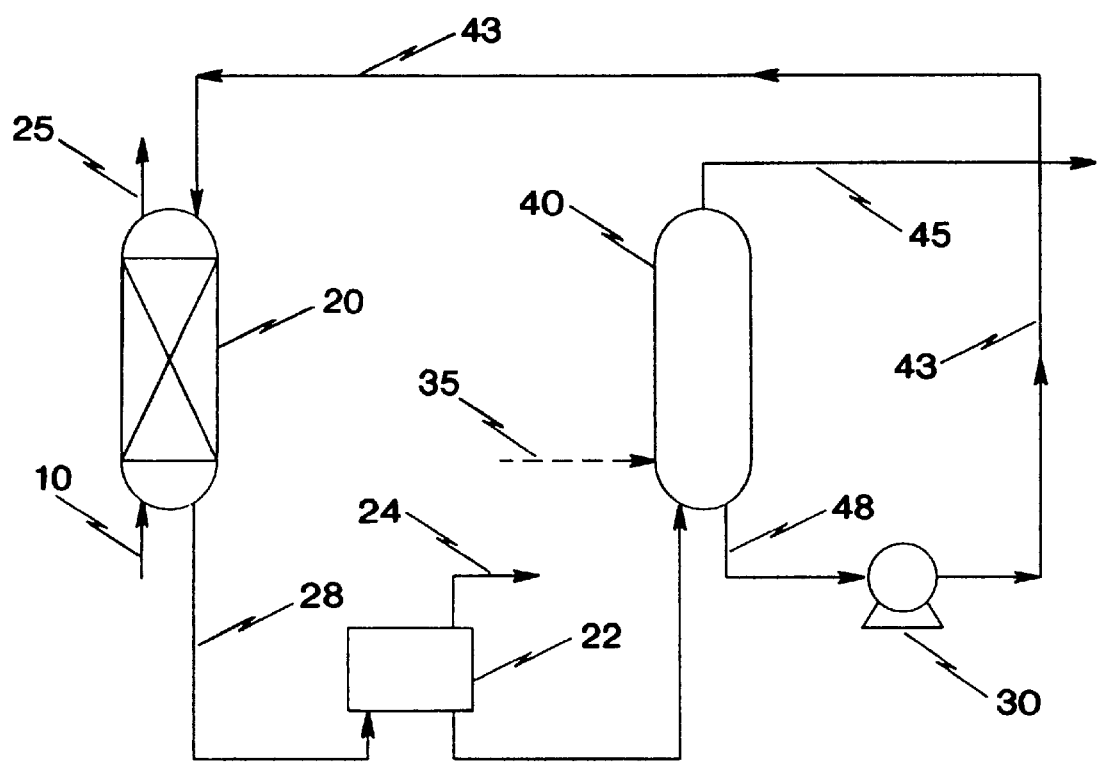
FIG. 4 is a schematic of the exemplary process depicted in FIG. 1 wherein a methane recovery flash tank is included.

FIG. 4 depicts the inclusion of a methane flash tank 22 equipped with a vent 24, by means of which a significant fraction of the dissolved methane may be recovered such that it can be used for energy to drive pumps or heat the desorption column or be retreated or recompressed and sold as sales gas.

Examples 1–31

A number of nitrogen-absorbing transition metal complexes were used in solution to demonstrate the utility of the invention to remove nitrogen from natural gas. All of the complexes were prepared in essentially the same manner, i.e., by reacting a salt of the transition metal with the appropriate ligand. In some cases further reaction steps were required to obtain a nitrogen-binding solution.

More specifically, the complexes of Examples 5, 10, 11, 16 and 18 were prepared by reacting $FeCl_2$ with two equivalents of a diphosphine ligand in ethanol or THF. Subsequent reaction of the $[FeCl_2(diphosphine)_2]$ complex with $NaBH_4$ and $NaBPh_4$ yielded the nitrogen-binding complex. The general reaction scheme is shown below:

$FeCl_2 + 2P_2 \rightarrow FeCl_2(P_2)_2$
$FeCl_2(P_2)_2 + NaBH_4 \rightarrow Fe(H)(Cl)(P_2)_2$
$Fe(H)(Cl)(P_2)_2 + NaBPh_4 \rightarrow [Fe(H)(P_2)_2]BPh_4$ where Ph is as defined above and $P_2$ is an alkyl or aryl diphosphino alkane or alkene ligand. The complex of Example 6 was prepared in this manner with the exception that the second reaction was not used.

The complexes of Examples 1–4, 9, 12, 14, 17, 19–20 and 31 were prepared in substantially the same manner as those of Examples 5, 10, 11, 16 and 18, except that the Fe(Cl) (H) $(P_2)_2$ complex was dissolved in a highly polar solvent such as water, ethylene glycol or triethylene glycol, sometimes in the presence of one equivalent of an acid with a weakly coordinating anion to adjust the solution pH or ionic strength.

The complexes of Examples 7 and 8 were prepared from $FeCl_2(P_2)_2$ complexes by treating the dichloride species sequentially with one equivalent of $NaBPh_4$, one equivalent of either dimethylphenylphosphine or 4-dimethylaminopyridine, and then another equivalent of $NaBPh_4$ as shown below.

$FeCl_2 (P_2)_2 + NaBPh_4 \rightarrow [Fe(Cl) (P_2)_2]BPH_4$
$[Fe(Cl)(P_2)_2]BPh_4 + L' \rightarrow [Fe(Cl)(L')(P_2)_2]BPh_4$
$[Fe(Cl)(L')(P_2)_2]BPh_4 + NaBPh_4 \rightarrow [Fe(L')(P_2)_2](BPh_4)_2$ where L' is dimethylphenylphosphine or 4-dimethylaminopyridine and Ph and $P_2$ are as defined above.

The complexes of Examples 22 and 24–30 were prepared by dissolving iron sulfate in the presence of two equivalents of the appropriate chelating ligand; for Examples 15 and 24–30 addition of one equivalent of monodentate phosphine was required for the solution to absorb nitrogen.

The complexes of Examples 13, 21 and 23 were prepared by reacting iron sulfate with two equivalents of the diphosphine, followed by reaction with sodium borohydride.

The complexes used are shown below.

$M_7[Fe(SPEPE),(H)](M=Li,Na,Cs,\frac{1}{2} Mg)$, $Na_7[(SAMSPE)_2(H)]$, $Na_7[Fe(SMPEPE)_2(H)]$ $[Fe(DEPE)_2(H)]BPh_4$, $[Fe(DEPE)_2Cl]BPh_4$, $[(Fe(DEPE)_2(DMAP)](BPh_4)_2$ $[Fe(DEPE)_2(PMe_2Ph)](BPh_4)_2$, $[Fe(DEPE)_2(H)]O_2CCH_2OH$ $[Fe(DPPP)_2(H)]BPh_4$, $[Fe(DPPET)_2(H)]BPh_4$ $[Fe(P_2glyme)_2(H)]O_3SCH_3$, $[Fe(DPGPB)_2(Cl)](SO_4)_{1/2}$, $[Fe(DPGPB)_2(PMe_2Ph)](SO_4)_{1/2}$ $[Fe(DIPHOS)_2 (H)]O_3SCH_3$, $[Fe(DIPHOS)_2(H)]BPh_4$ $[Fe(PPGPE)_2(H)]BPh_4$, $[Fe(HOBuPE)_2(H)(Cl)]$, $[Fe(HOPrOPE)_2 (H) (Cl)]$ $[Fe(DSPrPE)_2(H) (Cl)]$ $[Fe(HOBUPE)_2 (H_2O)_2]SO_4$, $[Fe(HOBUPE)_2(H) (SO_4)_{1/2}]$ $Na_6\{Fe(DTSA)_2[P(CH_2OH)_3]\}$ $[Fe(DEDTC)_2]PMe_2Ph$, $(Fe(DEGDTC)_2][P(CH_2OH)_3]$ $[Fe(DIAP)_2]PMe_2Ph$ $Na_2\{Fe(TDT)_2[P(CH_2OH)_3]\}$, $Na_2[Fe(TDT)_2(PMe_2Ph)]$, $Na_2[(Fe(TDT)_2(PMe_2Ph)]$ where SPEPE is 1,2-bis{di-[2-(4-sulfanato phenyl)ethyl]phosphino}ethane tetraanion, SAMSPE is 1,2-bis{di-[2-(4-sulfanato phenyl)propyl]phosphino}ethane tetraanion, SMPEPE is 1,2-bis-{di-[2-(2-methoxy-4-sulfanato)ethyl]phosphino}ethane tetraanion, DEPE is 1,2-bis-(diethylphosphino)ethane, DPPP is 1,2-bis-(diphenylphosphino)propane, DPPET is 1,2-bis-(diphenylphosphino)ethylene, $P_2$glyme is 1,2-bis{di[2-(2-(2-methoxy)ethoxy)ethoxy)ethyl]phosphino}ethane, DPGPB is 1,2-bis{di(1,2,3-trihydroxypropyl) phosphino]benzene, DIPHOS is 1,2-bis(diphenylphosphine)ethane, PPGPE is 1,2-bis[(phenyl-1,2,3-trihydroxypropyl)phosphino]ethane, HOBuPE is 1,2-bis[di-(4-hydroxybutyl)phosphino]ethane HOPrOPE is 1,2-bis [di-(3-hydroxypropyl)phosphino]ethane DSPrPE is 1,2-bis[di-(3-sulfonatopropyl)phosphino]ethane tetra anion DTSA is 2,3-dithiolate succinate tetraanion,
DEDTC is diethyldithio carbamate anion,
DEGDTC is di(2-hydroxy ethane)dithiocarbamate anion,
DIAP is (diisobutyl)dithiophosphinate anion,
TDT is 3,4-toluene dithiolate dianion, and
DMAP is 4-dimethylamino pyridine, and the solvents are water ($H_2O$), propylene carbonate (PC), ethylene glycol (EG) and triethylene glycol (TEG).

Absorption of nitrogen and methane by solutions of the transition metal complexes was demonstrated using a calibrated pressure apparatus to control the temperature, pressure, and volume of the solutions and gas. To measure the nitrogen or methane absorption by an absorbent solution, 5 to 20 mL of the solution was placed in a chamber. Nitrogen or methane was then introduced at a pressure of from 50 to 1000 psia into the chamber from a 15 mL stainless steel reservoir and the gas absorbed by the solution was calculated from measurement of the pressure and volume of the remaining gas, taking into account the amount of nitrogen absorbed by the pure solvent alone. In the examples where methane absorption was determined, the volume of methane absorbed did not differ significantly from physical solubility of methane in the solvent. In all cases the absorption/desorption cycle was repeated at least five times to verify the stability of the sorption material.

The results of such nitrogen absorption tests at 150 psig and 20° C. with the absorbent solutions of the present invention are shown in Table 4. In those cases where the absorbed nitrogen was desorbed from the absorbent solution by decreasing the nitrogen partial pressure to 1 atmosphere, the same is indicated by the numeral "1" in the "Desorption Conditions" column, whereas the numeral "2" is used in the same column to denote desorption by decreasing the nitrogen partial pressure to 0.1 atmosphere and increasing the temperature to between 40° and 120° C. "$N_2/CH_4$ Selectivity" is as the calculated ratio of $N_2$ absorbed to $CH_4$ absorbed, assuming 15 vol % $N_2$ and 85 vol % $CH_4$ in a feed stream at 1000 psig, normalized to their respective final partial pressures.

TABLE 4

| Ex. No. | Complex | Solvent (gM) | $N_2$ Capacity* | $N_2/CH_4$ Selectivity | Desorption Conditions |
|---|---|---|---|---|---|
| 1 | $Na_7[Fe(SPEPE)_2(H)]$ | $H_2O$(1.0) | 0.5 | 5.75 | 1 |
| 2 | $Li_7[Fe(SPEPE)_2(H)]$ | $H_2O$(1.0) | 0.5 | 5.75 | 1 |
| 3 | $Na_7[Fe(SAMSPE)_2(H)]$ | $H_2O$(0.75) | 0.2 | 2.31 | 1 |
| 4 | $Na_7[Fe(SMPEPE)_2(H)]$ | $H_2O$(1.0) | 0.27 | 4.61 | 1 |
| 5 | $[Fe(DEPE)_2(H)]BPh_4$ | PC(0.30) | 0.5 | 0.32 | 2 |
| 6 | $[Fe(DEPE)_2(Cl)]BPh_4$ | PC(0.30) | 0.3 | 0.20 | 1 |
| 7 | $[Fe(DEPE)_2(DMAP)][BPh_4]_2$ | PC(0.25) | 0.05 | 0.03 | 1 |
| 8 | $[Fe(DEPE)_2(PMePh_2)][BPh_4]_2$ | PC(0.25) | 0.1 | 0.09 | 1 |
| 9 | $[Fe(DEPE)_2(H)]O_2CCH_2OH$ | $H_2O$(0.4) | 0.3 | 1.61 | 1 |
| 10 | $[Fe(DPPP)_2(H)]BPh_4$ | PC(0.25) | 0.01 | 0.03 | 1 |
| 11 | $[Fe(DPPET)_2(H)]BPh_4$ | PC(0.1) | 0.1 | 0.03 | 1 |
| 12 | $[Fe(P_2glyme)_2(H)]O_3SCH_3$ | $H_2O$(0.5) | 0.2 | 1.15 | 1 |
| 13 | $[Fe(DPGPB)_2(H)](SO_4)_{½}$ | $H_2O$(0.65) | 0.08 | 0.58 | 1 |
| 14 | $[Fe(DPGPB)_2(H)](SO_4)_{½}$ | EG(0.5) | 0.08 | 0.23 | 1 |
| 15 | $[Fe(DPGPB)_2(PMe_2Ph)](SO_4)_{½}$ | PC(0.25) | 0.25 | 0.17 | 1 |
| 16 | $[Fe(DIPHOS)_2(H)]BPh_4$ | PC(0.1) | 0.5 | 0.14 | 2 |
| 17 | $[Fe(HOBuPE)_2(H)(Cl)]$ | $H_2O$(0.7) | 0.5 | 4.0 | 1 or 2 |
| 18 | $[Fe(PPGPE)_2(H)]BPh_4$ | PC(0.25) | 0.1 | 0.09 | 1 |
| 19 | $[Fe(HOPrOPE)_2(H)(Cl)]$ | $H_2O$(0.8) | 0.5 | 4.6 | 1 |
| 20 | $[Fe(HOBuPE)_2(H)(Cl)]$ | TEG (0.5) | 0.5 | 1.5 | 1 or 2 |
| 21 | $[Fe(HOBuPE)_2(H)](SO_4)_{½}$ | $H_2O$ (0.5) | 0.5 | 2.9 | 1 or 2 |
| 22 | $[Fe(HOBuPE)_2(H_2O)_2]SO_4$ | $H_2O$(0.8) | 0.15 | 1.4 | 2 |
| 23 | $[Fe(HOBuPE)_2(H)](SO_4)_{½}$ | TEG (0.5) | 0.5 | 1.5 | 1 or 2 |
| 24 | $Na_6\{Fe(DTSA)_2[P(CH_2OH)_3]\}$ | $H_2O$(0.25) | 0.02 | 0.06 | 1 |
| 25 | $[Fe(DEDTC)_2]PMe_2Ph$ | PC(0.3) | 0.07 | 0.06 | 1 |
| 26 | $[Fe(DEGDTC)_2]P(CH_2OH)_3$ | $H_2O$(0.5) | 0.02 | 0.12 | 1 |
| 27 | $[Fe(DIAP)_2]PMe_2Ph$ | PC(0.25) | 0.04 | 0.12 | 1 |
| 28 | $Na_2[Fe(TDT)_2(PMe_2Ph)]$ | PC(0.5) | 0.2 | 0.29 | 1 |
| 29 | $Na_2[Fe(TDT)_2(PMe_2Ph)]$ | $H_2O$(0.5) | 0.04 | 0.23 | 1 |
| 30 | $Na_2\{Fe(TDT)_2[P(CH_2OH)_3]\}$ | $H_2O$(0.75) | 0.01 | 0.12 | 1 |
| 31 | $[Fe(DSPrPE)_2(H)(Cl)]$ | $H_2O$(0.7) | 0.5 | 4.1 | 1 |

*mol $N_2$/mol complex at 150 psig

EXAMPLE 32

Figure 6:
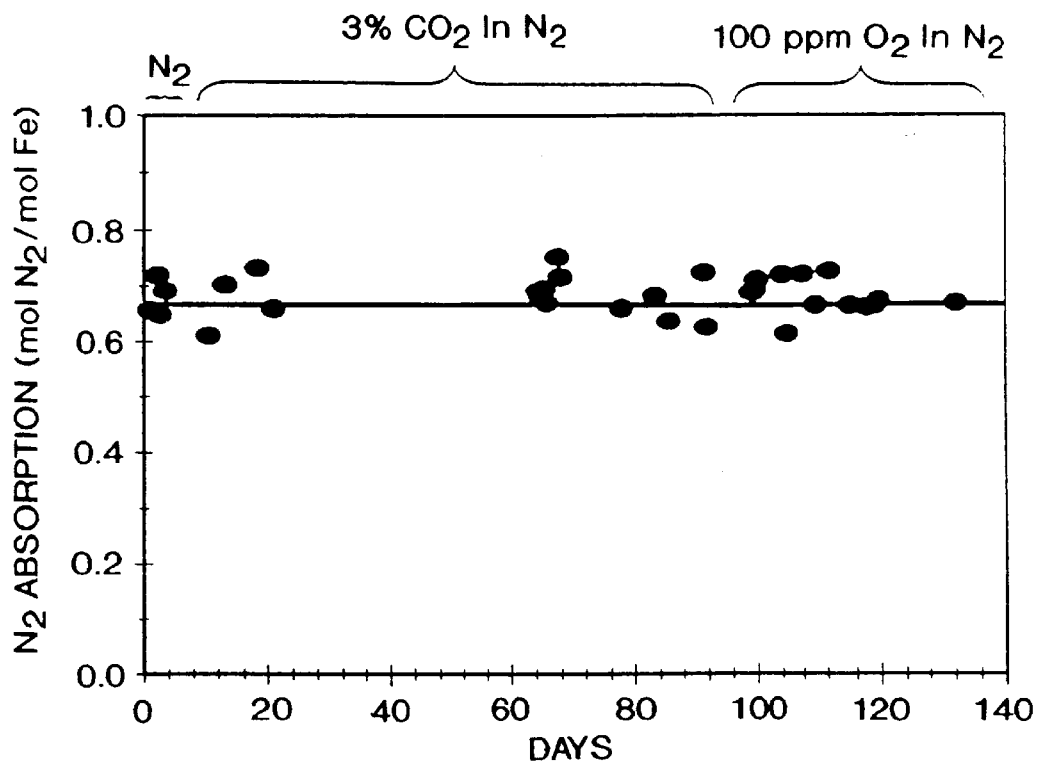
FIG. 6 is a graph illustrating the stability of a sorption material of the present invention.

To demonstrate that repeated absorption and desorption of nitrogen does not diminish the capacity of an absorbent of the invention, a 0.1 M aqueous solution of $Na_7[Fe(SPEPE)_2(H)]$ was repeatedly cycled through nitrogen absorption and desorption, as shown in FIG. 6, as a function of time. As is apparent from FIG. 6, there was no substantial diminution of nitrogen absorption capacity, even after approximately 100 cycles over the course of five days.

EXAMPLE 33

Example 32 was substantially repeated over 30 days with the exception that the complex was $[Fe(DEPE)_2(Cl)]BPh_4$ and the solvent was PC. No diminution of nitrogen sorption capacity was observed.

EXAMPLE 34

To demonstrate that the presence of $CO_2$, a naturally occurring contaminant in natural gas, does not adversely affect the nitrogen sorption capacity of an absorbent of the invention, a 0.1 M aqueous solution of $Na_7[Fe(SPEPE)_2(H)]$ was repeatedly cycled through nitrogen absorption/ desorption cycles in the presence of 3% $CO_2$ over 100 days. The nitrogen binding capacity is shown in FIG. 6 as a function of time. No diminution of nitrogen sorption capacity was observed.

EXAMPLE 35

Example 34 was substantially repeated with the exception that the complex was [Fe(DEPE)$_2$(Cl)]BPh$_4$, the solvent was PC and time was 30 days. No diminution of nitrogen sorption capacity was observed.

EXAMPLE 36

To demonstrate that the presence of $H_2S$, another naturally occurring contaminant in natural gas, does not adversely affect the nitrogen-binding capacity of the sorption material of the present invention, a 0.1 M solution of [Fe(DEPE)$_2$(Cl)]BPh$_4$ in PC was stored in the presence of 50 ppm $H_2S$ over four days. No diminution of nitrogen sorption capacity was observed following the exposure to $H_2S$.

EXAMPLE 37

Example 36 was substantially repeated with the exception that the complex was [Fe(DEPE)$_2$(H)]BPh$_4$ in PC and exposure was continued over 15 hours. No diminution of nitrogen sorption capacity was observed.

EXAMPLE 38

To demonstrate the thermal stability of the sorption material a solution of [Fe(DEPE)$_2$(Cl)]BPh$_4$ in PC was heated at 70° C. over 14 days. No diminution of nitrogen sorption capacity was observed over the course of the heat treatment.

EXAMPLE 39

Example 32 was substantially repeated except the absorbent was 0.4 M aqueous solution of [Fe(HOBuPE)$_2$(H$_2$O)$_2$]SO$_4$ and the sorption/desorption cycles were continued over eight days, again with no noticeable diminution of absorption capacity.

EXAMPLE 40

Figure 5:
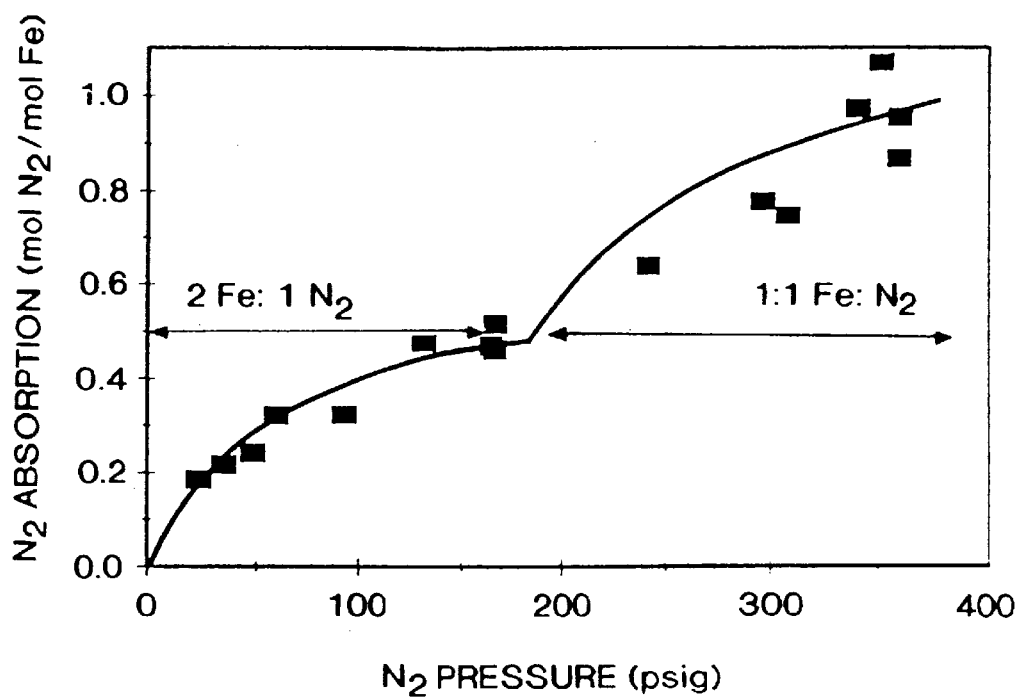
FIG. 5 is a graph illustrating the nitrogen-binding capacity of a sorption material of the present invention as a function of pressure.

A 0.1 M aqueous solution of the complex Na$_7$[Fe(SPEPE)$_2$(H)] was tested for nitrogen absorption and desorption as a function of pressure. As shown in FIG. 5, which comprises a graph of the results, there appears to be formation of a 2:1 Fe:$N_2$ complex at lower pressures, which is converted to a 1:1 Fe:$N_2$ complex at higher pressures, based upon the observed absorption of 0.5 equivalent of $N_2$ absorbed per equivalent of Fe in solution at low nitrogen partial pressures and 1.0 equivalent at higher nitrogen partial pressures.

EXAMPLE 41

Low concentrations of oxygen may be encountered in natural gas deposits or may be observed upon start-up and shutdown. To demonstrate that the presence of oxygen does not adversely affect the nitrogen sorption capacity of an absorbent of the invention, a 0.1 M aqueous solution of Na$_7$[Fe(SPEPE)$_2$(H)] was repeatedly cycled through nitrogen absorption/desorption cycles in the presence of 100 ppm oxygen over 35 days. The nitrogen-binding capacity is shown as part of FIG. 6; as is apparent, no diminution of sorption capacity took place.

EXAMPLE 42

Example 41 was substantially repeated except that the absorbent was 0.4 M aqueous [Fe(HOBUPE)$_2$ (H$_2$O)$_2$]SO$_4$ and the absorption/desorption cycles were continued over 25 days, again with no noticeable diminution of nitrogen sorption capacity.

EXAMPLE 43

To demonstrate that a coordinatively saturated transition-metal complex can serve as a precursor to the actual $N_2$-binding compound, a 0.5 M triethylene glycol solution of [Fe(HOBuPE)$_2$($\eta^2$—H$_2$) (H)](SO$_4$)$_{1/2}$ was exposed to 55 psia pure $N_2$ in a closed container. During the experiment no pressure decrease was noted. Evaluation of the headgas over the solution following this experiment showed that 0.5 mol $H_2$/mol Fe had been produced. Thus, $N_2$ had displaced $H_2$ to form the $N_2$-bound compound.

The terms and expressions employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A nitrogen-absorbing and -desorbing composition consisting essentially of a solvent with a solubility parameter of $\geq 20$ MPa$^{1/2}$ and a transition metal complex, said complex comprising (a) a metal selected from Cr, W, Mn, Fe, Co and Ni;
   (b) at least one reversibly bound molecular nitrogen ligand; and
   (c) at least one other monodentate or multidentate ligand that, together with said at least one molecular nitrogen ligand provides four, five or six coordinating atoms to the metal wherein said transition metal complex is present in a concentration of $\geq 0.1$ M in said solvent and said complex enhances the nitrogen solubility therein relative to the nitrogen solubility in said solvent alone.

2. The composition of claim 1 wherein said solvent is selected from the group consisting of water, organic acids, esters, alcohols, glycols, glycolic ethers, diols, ethers, amines, amides, lactams, nitriles, nitro-substituted alkanes, carbonates, phosphates, sulfoxides, sulfides, sulfates, nitrogen-containing heterocycles, oxygen-containing heterocycles, sulfur-containing heterocycles and mixtures thereof.

3. The composition of claim 1 wherein said solvent is chosen so as to render methane solubility in the solution $\leq 0.02$ M/atm at 20° C.

4. The composition of claim 1 wherein said at least one other ligand is selected from the group consisting of phosphines, phosphites, phosphides, hydride, thiolates, thiols, thioethers, thiocarbarnates, dithiocarbamates, thiocarbonates, dithiocarbonates, trithiocarbonates, dithiolenes, phosphinates, thiophosphinates, dithiophosphinates, diketonates, catecholates, carboxylates, thiocarboxylates, dithiocarboxylates, amines, amides, pyridines, imidazoles, pthalocyanines, porphyrins, halogens, carbanions and hybrids thereof.

5. The composition of claim 1 wherein said transition metal is Fe; said at least one other ligand is selected from phosphines and phosphites, and said solvent is selected from the group consisting of water, alcohols, glycols, glycolic ethers, diols, ethers, polyethers, carbonates, phosphates, sulfoxides, sulfides, and mixtures thereof.

6. The composition of claim 1, including at least one agent selected from the group consisting of an antioxidant, an anti-foaming agent, a surfactant, a buffer and a corrosion inhibitor.

7. The composition of claim 1 wherein said transition metal complex is cationic and is rendered hydrophilic by the cation's associated anion where the anion is selected from the group consisting of halogens, sulfonates, sulfinates, selenates, alkoxides, phonoxides, carbonates, bicarbonates, carboxylates, sulfates, bisulfates, phosphates, perchlorates, nitrates, tetrasubstituted borate's, tetrasubstituted aluminates, hexasubstituted phosphates, hexasubstituted arsenates and hexasubstituted stibnates.

8. The composition of claim 1 wherein said solvent is selected from the group consisting of water, ethylene carbonate, propylene carbonate, ethylene glycol, propylene glycol, triethylene glycol, glycolic oligomers and their alkyl ethers, and mixtures thereof.

9. The composition of claim 8 wherein said solvent is water.

10. The composition of claim 1 wherein said at least one other ligand is selected from the group consisting of phosphines, phosphites, phosphides, amines and amides.

11. The composition of claim 10 wherein said transition metal complex is hexacoordinate and said at least one other ligand is selected from the group consisting of phosphines, phosphites and phosphides.

12. The composition of claim 1 wherein said transition metal complex is hexacoordinate and said at least one other ligand comprises two bidentate ligands.

13. The composition of claim 12 wherein said at least one other ligand is selected from the group consisting of a hydride, a halide and a tetrahydridoborate.

14. The composition of claim 12 wherein said transition metal is Fe.

* * * * *

UNITED STATES PATENT AND TRADEMARK OFFICE
CERTIFICATE OF CORRECTION

PATENT NO. : 6,136,222
DATED : October 24, 2000
INVENTOR(S) : Friesen et al.

It is certified that error appears in the above-identified patent and that said Letters Patent is hereby corrected as shown below:

Column 1,
Line 49, change "PPh$_2$)$_2$" to read -- PPh$_2$)$_2$) --
Line 59, change "(DIPHOS)$_2$" to read -- (DIPHOS)$_2$] --

Column 3,
Line 12, change "preferably $\leq$0.1 atm," to read -- preferably $\leq$0.1M/atm, --
Line 45, delete the second period (.) after "phosphates."

Column 8,
Line 21, change "H$^{31}$" to read -- H$^-$ --

Column 16,
Line 67, delete the signs "<→" and substitute therefore "↔"

Column 18,
Line 1, change "CH$_2$)$_2$P-R-P" to read -- CH$_2$)$_2$P-R$^1$-P --

Column 19,
Line 19, delete the hyphen (-) between "or" and "combination"
Line 52, delete the hyphen (-) between "as" and "nitrogen"

Column 20,
Line 54, delete the hyphen (-) between "temperature" and "relative"

Column 22,
Line 32, insert a comma (,) after "BPh$_4$"
Line 43, delete parenthesis before "Fe"

UNITED STATES PATENT AND TRADEMARK OFFICE
CERTIFICATE OF CORRECTION

PATENT NO. : 6,136,222
DATED : October 24, 2000
INVENTOR(S) : Friesen et al.

It is certified that error appears in the above-identified patent and that said Letters Patent is hereby corrected as shown below:

Column 26,
Line 50, change "and phosphites," to read -- and phosphites;" --
Line 51, delete "thiocarbarnates" and substitute -- thiocarbamates --

Column 27,
Line 5, change "phonoxides" to read -- phenoxides --

Signed and Sealed this

Thirtieth Day of April, 2002

Attest:

JAMES E. ROGAN
Attesting Officer	Director of the United States Patent and Trademark Office